(12) United States Patent
Bernay et al.

(10) Patent No.: US 9,658,141 B2
(45) Date of Patent: May 23, 2017

(54) STATION FOR THE SELECTIVE UNCAPPING OF GEL CARDS

(75) Inventors: Sébastien Bernay, Ecoche (FR); Jean-Michel Brisebrat, Villers (FR); Frédéric Buffière, Pessac (FR)

(73) Assignees: Bio-Rad Innovations, Mames la Coquette (FR); DiaMed GmbH, Cressier (CH)

( * ) Notice: Subject to any disclaimer, the term of this patent is extended or adjusted under 35 U.S.C. 154(b) by 607 days.

(21) Appl. No.: 14/004,111

(22) PCT Filed: Mar. 9, 2012

(86) PCT No.: PCT/FR2012/050505
§ 371 (c)(1),
(2), (4) Date: Dec. 16, 2013

(87) PCT Pub. No.: WO2012/120246
PCT Pub. Date: Sep. 13, 2012

(65) Prior Publication Data
US 2014/0093972 A1    Apr. 3, 2014

(30) Foreign Application Priority Data
Mar. 10, 2011   (FR) ...................................... 11 51973

(51) Int. Cl.
*G01N 1/28* (2006.01)
*B67B 7/00* (2006.01)
(Continued)

(52) U.S. Cl.
CPC .................. *G01N 1/28* (2013.01); *B67B 7/00* (2013.01); *B67B 7/38* (2013.01); *G01N 27/62* (2013.01);
(Continued)

(58) Field of Classification Search
CPC ........................................................ G01N 1/28
(Continued)

(56) References Cited

U.S. PATENT DOCUMENTS

2002/0166790 A1* 11/2002 Aylward ................. B65B 11/50
206/531
2003/0041560 A1*  3/2003 Kemnitz ............... B65B 7/2828
53/331.5
(Continued)

FOREIGN PATENT DOCUMENTS

FR   WO 2010116069 A2 * 10/2010   ......... G01N 35/1079
WO   WO 2006/094388 A1    9/2006
(Continued)

OTHER PUBLICATIONS

Google Translation of WO 2010116069 A2 obtained Mar. 15, 2016.*
(Continued)

*Primary Examiner* — Christopher A Hixson
*Assistant Examiner* — Emily Berkeley
(74) *Attorney, Agent, or Firm* — Bookoff McAndrews, PLLC

(57) ABSTRACT

The invention relates to a station for uncovering a receptacle comprising a body in which a plurality of adjacent holes, initially sealed by a cover, are formed. The station comprises at least one cutting member for making at least one cut in the cover between two adjacent holes, so as to form at least one cover portion closing off at least one of the holes of the receptacle, i.e., the selected hole; and at least one heating gripping device which is arranged so as to heat and remove said cover portion, thereby opening the selected hole.

11 Claims, 5 Drawing Sheets

(51) Int. Cl.
*G01N 27/62* (2006.01)
*G01N 35/04* (2006.01)
*G01N 35/02* (2006.01)

(52) U.S. Cl.
CPC ... *G01N 35/026* (2013.01); *G01N 2035/0405* (2013.01); *G01N 2035/0436* (2013.01); *Y10T 436/25* (2015.01); *Y10T 436/25875* (2015.01)

(58) Field of Classification Search
USPC .......................................................... 436/181
See application file for complete search history.

(56) References Cited

U.S. PATENT DOCUMENTS

| | | | |
|---|---|---|---|
| 2005/0160704 A1* | 7/2005 | Miksch | B65B 69/00 53/492 |
| 2006/0188404 A1* | 8/2006 | Gjerde | B01L 3/50853 422/400 |
| 2007/0172393 A1* | 7/2007 | Beer | B01L 3/50853 422/400 |
| 2012/0051975 A1 | 3/2012 | Buffiere et al. | |

FOREIGN PATENT DOCUMENTS

| | | |
|---|---|---|
| WO | WO 2010/007709 A1 | 1/2010 |
| WO | WO 2010/116069 A2 | 10/2010 |

OTHER PUBLICATIONS

My Contact Lens, "My Contact Lenses: blister packing", May 30, 2008, 2 pages, (https://mycontactlens.wordpress.com/2008/05/30/blister-packing/).

My Contact Lens, "My Contact Lenses: saline on a blister pack", May 30, 2008, 2 pages, (https://mycontactlens.wordpress.com/2008/05/30/saline-on-a-blister-pack/).

International Search Report for corresponding International Application No. PCT/FR2012/050505, mailed on May 9, 2012, 4 pages.

* cited by examiner

STATION FOR THE SELECTIVE UNCAPPING OF GEL CARDS

CROSS-REFERENCE TO RELATED APPLICATIONS

This application is a National Stage filing under 35 U.S.C. §371 of International Application No. PCT/FR2012/050505, filed Mar. 9, 2012, which claims priority to French Patent Application No. FR1151973, filed Mar. 10, 2011, the contents of each of which are incorporated by reference herein.

FIELD OF THE INVENTION

The present invention relates to the field of apparatuses for performing biological or medical analyses.

BACKGROUND OF THE INVENTION

Traditionally, such apparatuses, also called automated analyzer, make it possible to automate certain protocols, for example such as the distribution of liquids in gel cards. This protocol consists of pouring a predetermined quantity of liquid using a liquid distributing device into a reaction hole of a gel card generally containing one or more reagents. This liquid may for example be a blood sample, or any other type of human sample.

In a known manner, a gel card is a receptacle including a body in which one or more reaction holes are formed in which the biological reactions take place.

Traditionally, the holes of the gel card are initially covered by a cover that is sealed to the body. Most often, this cover is made up of a thin strip of aluminum.

Generally, the operation for distributing liquids in the reaction holes is carried out by piercing the cover using a liquid distribution device provided with a needle so as to open one or more holes. Next, the liquid is poured into the hole(s) using that same needle.

One drawback is that repeating the metal cover piercing operation destroys the tips of the needles. The latter must therefore be disassembled and changed regularly, which represents a non-negligible cost and furthermore requires stopping the machine.

Another drawback appears during the use of gel cards having non-identical reaction holes, i.e., containing different reagents. In that case, it is generally necessary to wash the needles between each liquid distribution so as to avoid contamination between the holes of said gel card. By passing through the cover in order to open a first hole containing the first reagent, the needle may be soiled by droplets of first reagent that may be attached on an inner face of the cover. If the needle is not rinsed, it risks transporting the first reagent into a second hole containing a second reagent different from the first reagent, and causing contamination of the second reagent.

BRIEF DESCRIPTION OF THE INVENTION

One aim of the present invention is to resolve these drawbacks by proposing a solution for opening the holes without piercing the cover.

The present invention therefore relates to a station for the uncovering of a receptacle including a body in which several adjacent holes initially sealed by a cover are formed. Preferably, the adjacent holes are initially heat-sealed by a cover. In that case, the cover is preferably heat-sealed to the receptacle. It may also simply be glued to the receptacle.

It is specified that this uncovering station is first and foremost, but not necessarily, designed to be used with an analysis machine, the receptacles then preferably being gel cards.

According to the invention, the uncovering station according to the invention includes:
 at least one cutting member for making at least one cut in the cover between two adjacent holes, so as to form at least one cover portion covering at least one of the holes of the receptacle, being a selected hole;
 at least one heating gripping device that is arranged to heat and remove said cover, thereby opening the selected hole.

"Selected hole" refers to a hole that is covered by the cover portion that will be removed by the heating gripping device.

After opening the selected hole, the needle of the liquid distribution device is inserted therein so as to pour the liquid into the hole. Thus, the invention makes it possible to do away with the step for piercing the cover, which makes it possible to do away with the damage to the end of the needle of the liquid distribution device. Furthermore, inasmuch as the cover portion has been removed, the aforementioned risk of contamination is avoided, owing to which the washing operation between each liquid distribution may advantageously be eliminated or done less frequently.

It is specified that within the meaning of the invention, the cut may be formed over all or part of the width of the cover, and over all or part of the thickness of the cover, the cut having to be sufficient to allow the gripping device to remove the cover portion. Preferably, the cut will be made over the entire thickness and the entire width of the cover so as to isolate the cover portion from the rest of the cover.

Generally, the body of the receptacle is made from plastic and the cover is sealed to the bodies using a heat-sealing film or a glue.

It will be understood that the heat given off by the gripping device makes it possible to unglue or unweld the cover portion initially sealed to the body of the receptacle, in particular when said cover portion is initially heat-sealed, thermofused or simply glued to the body of the receptacle, by melting the heat-sealing film or the glue positioned between the cover and the body of the receptacle. After the heating step, or concomitantly therewith, the gripping device removes a portion of the cover outside the body, for example by peeling it.

The heating gripping device makes it possible to melt this heat-sealing film or this glue, for example by applying a temperature of approximately 200° C. for a long enough length of time to obtain melting.

The heat transfer between the heating gripping device and the plastic material is ensured owing to the conductive properties of the component material of the cover, which is preferably metal.

After the cover portion is removed by the gripping device, the selected hole that was initially covered by said cover portion is open. Furthermore, the rest of the cover remains heat-sealed to the body of the receptacle while covering the non-selected holes.

Preferably, the gripping device comes into contact with the cover while exerting a predetermined pressure thereon for a predetermined length of time, so as to ensure good homogeneity of the heat transfer.

Hereafter, it will be understood that one major interest of the invention lies in allowing the selective opening of one or more holes, i.e., the reaction holes one wishes to use (the selected holes), the other holes advantageously remaining covered for a future reuse of the receptacle, and in order to avoid drying of the open reaction holes not intended to be used.

Furthermore, the invention makes it possible to open one or more holes that are not necessarily adjacent.

Preferably, but not necessarily, the holes of the receptacle are aligned in a single row.

It will be understood that opening an end hole, i.e., one of the two situated at the two ends of the row, requires a single cut formed between said end hole and the hole adjacent to it. On the other hand, opening a selected hole positioned between the two end holes requires producing two cuts made between the selected hole and each of the two holes adjacent to the selected hole.

Advantageously, the station according to the invention includes a plurality of cutting members, each of the cutting members being able to produce a cut in the cover between the two adjacent holes so as to form one or more cover portions covering one or more holes. Preferably, as many cover portions are formed as there are holes. However, the cutting means may be arranged to form a number of cover portions corresponding to the number of holes selected.

One interest lies in being able to produce several cover portions at the same time, owing to which the performance speed of the uncovering operation is improved.

For example, if the receptacle is a gel card including six holes, it is then possible to form six cover portions simultaneously using five cutting members, for example made up of five blades or saws.

Advantageously, the station according to the invention includes a plurality of gripping devices that can be moved independently of one another, each of the gripping devices having an idle position in which said gripping device is heated by a heating device, and a working position in which said heating gripping device is brought to bear against the or one of the cover portion(s).

Thus, the invention makes it possible to remove several cover portions at once, i.e., to open several selected holes in a single operation, said holes not necessarily being adjacent.

Preferably, but not exclusively, as many gripping devices are provided as there are holes in the receptacle.

Furthermore, the station advantageously includes a selection mechanism for selecting the gripping device(s) needing to be moved toward the working position, and a movement device for moving said selected gripping device(s) toward the working position.

According to one preferred embodiment, the selection mechanism is arranged so as not to allow the movement of the gripping devices associated with the holes that are not selected, i.e., that are not designed to be opened.

For example, the movement device includes a plate, each gripping device is fastened to the plate using a spring designed to exert a pressure force on the gripping device oriented toward the body of the receptacle, and the selection mechanism is arranged to prevent the movement, for example vertical movement, of the gripping devices that are not selected.

Advantageously, the heating device includes a fixed heating baseplate and, in the idle position, each gripping device is in contact with said heating baseplate.

It will therefore be understood that each heating gripping device is heated by the heating baseplate when said device is in the idle position. One interest lies in keeping the gripping devices at a sufficient temperature to allow ungluing of the cover portions, in particular the gripping devices that are not used for several hole opening sequences.

Such an arrangement in particular makes it possible to avoid the downtime resulting from the heating time of the gripping devices not in use and thereby improves the efficacy of the uncovering station.

Preferably, each gripping device comprises means for gripping one of the cover portions, and the station furthermore includes at least one discharge member for expelling said cover portion gripped by the gripping device. One interest of these means lies in avoiding the flash resulting from melting the thermoplastic welding material, which may form plastic threads connected to the cover portion that would solidify again upon removal of said cover portion.

It will therefore be understood that the means for gripping one of the cover portions make it possible to facilitate the removal of said cover portion. Said means make it possible to perform a vertical removal during the raising of the gripping device or to facilitate the removal operation by peeling through transverse movements of the receptacle relative to the gripping devices.

Preferably, the discharge member includes a rod, preferably stationary, around which the gripping device slides, said rod being arranged to expel the cover portion when the gripping device is returned to the idle position. Another function of the rod is to guide the movement of the gripping device.

Thus, when the gripping device is in the working position, the rod is preferably housed in the gripping device so as not to touch the cover portion. However, after the cover removal operation, when the gripping device is returned to the idle position, the latter generally takes the cover portion with it. The rod then protrudes outside the gripping device so as to free the cover portion.

According to another aspect of the invention, the uncovering station further includes means for verifying whether the selected hole has been correctly opened.

To that end, sensors are provided, such as optical sensors, preferably one per hole.

Furthermore, the station includes an ionizer to ionize the selected hole(s) after opening thereof. The ionization of the holes makes it possible to eliminate the electrostatic charges contained in the holes that are generally the source of the appearance of liquid droplets on the inner surface of the holes.

The invention also relates to a biological sample analysis installation including an uncovering station according to the invention that is designed to uncover the cards including reaction holes.

The present invention also relates to a method for uncovering a receptacle including a body in which several adjacent holes initially sealed by a cover are formed, in which:

at least one cut is made in the cover between two adjacent holes so as to form at least one cover portion covering at least one of said holes, being a selected hole;

the cover portion is heated so as to be unglued from the body;

the cover portion is removed from the body, the selected hole being thereby opened.

This method is advantageously carried out using the uncovering station according to the invention.

Advantageously, according to the method:

several cover portions are formed in the cover, said cover portions covering some of the holes, being the selected holes, said cover portions are heated so as to unglue them from the body, said cover portions are removed from the body, the selected holes being thereby opened.

Preferably, after the uncovering operation, the selected holes are ionized after being opened, then, still preferably, it is verified that the selected holes have been correctly opened.

BRIEF DESCRIPTION OF THE DRAWINGS

The invention will be better understood, and the advantages thereof will better appear, upon reading the following detailed description of one embodiment shown non-limitingly. The description refers to the drawings, in which.

DETAILED DESCRIPTION OF THE INVENTION

Figure 1:
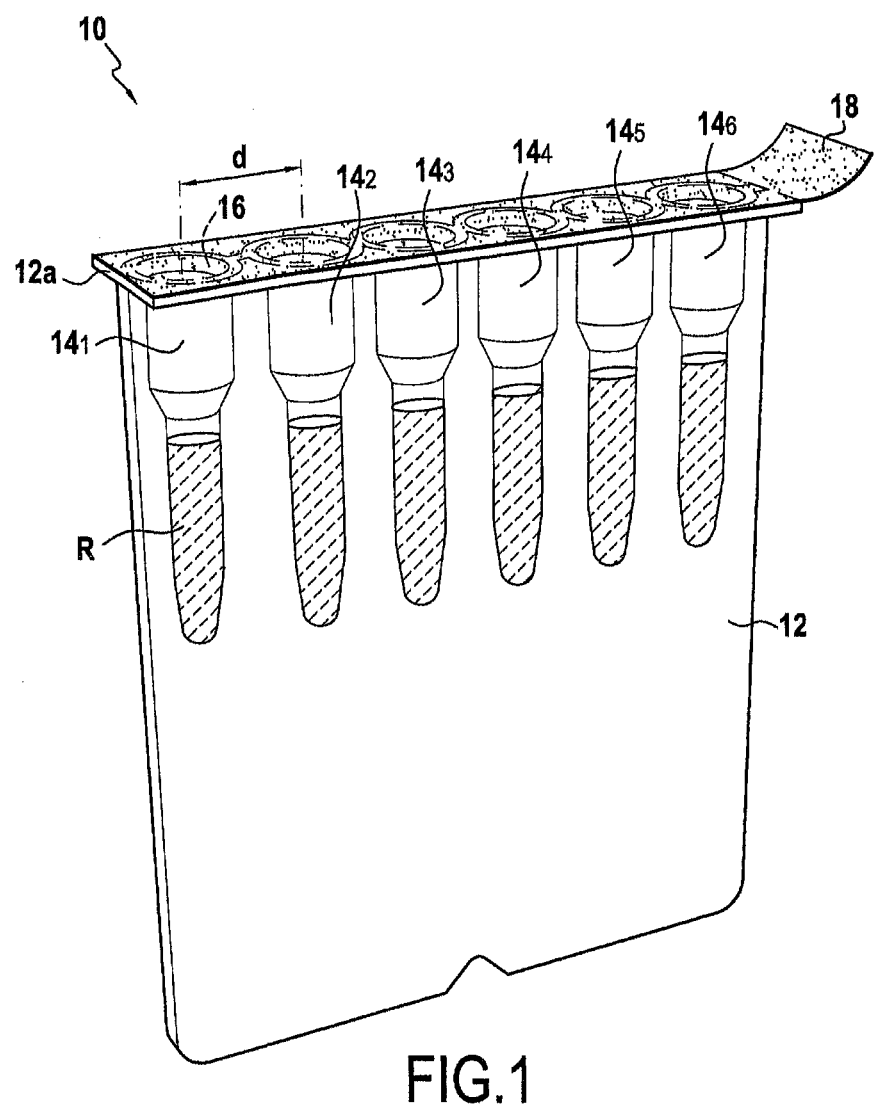
FIG. 1 shows an example of a receptacle, i.e., an empty gel card including six reaction holes aligned in a single row, designed to be used with the uncovering station according to the invention.

The receptacle 10 shown in FIG. 1 includes a plastic body 12 in which several reaction holes 14 are formed, in this case six holes referenced $14_1$, $14_2$, $14_3$, $14_4$, $14_5$, $14_6$, which are adjacent and positioned in a single row. Each of the holes contains a reagent R that may be identical to or different from the reagent contained in the neighboring hole. Such a receptacle is well known and is generally called a "gel card".

In reference to FIG. 1, one can see that the holes 14 emerge in an upper wall 12a of the gel card. These holes 14 therefore have openings 16 formed in the upper wall 12a of the gel card, said openings 16 initially being covered by a cover 18. In this example, the cover 18 consists of a thin strip of aluminum that is heat-sealed to the upper wall 12a of the body 12 of the gel card 10, for example using a heat-sealing film or a glue. The distance d between holes corresponds to the distance between the axes of symmetry of two adjacent holes.

As shown in this FIG. 1, the thickness of the gel card 10 is substantially smaller than its other two dimensions.

In light of FIGS. 2 to 7, an uncovering station 100 according to the invention will be described that is designed to open one or more holes 14 of the gel card 10 previously described. An uncovering method, also according to the invention, implemented by the station 100 will also be described.

In this example, the uncovering station 100 includes a housing 102 from which two horizontal arms 104 extend. Each of said two arms is provided with a longitudinal slot 106, the two slots 106 being designed to receive the edges of an intake tray 108. In reference to FIGS. 2 and 3, it will be understood that the intake tray 108 can slide in a horizontal plane while being guided in translation by the slots 106.

Figure 2:
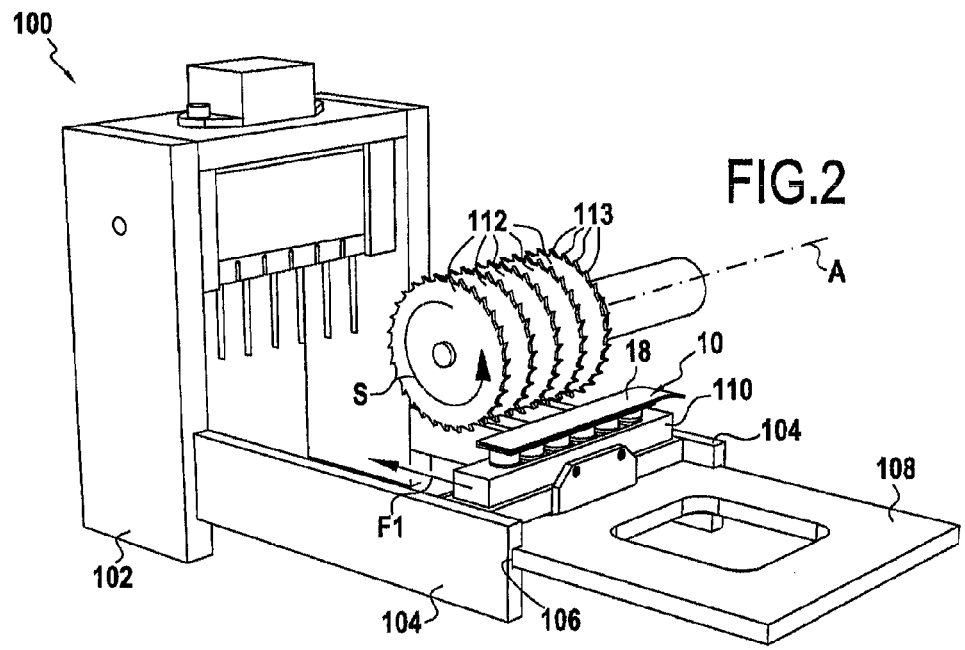
FIG. 2 is a perspective view of an uncovering station according to the invention, and illustrates the step during which the cover of the gel card of FIG. 1 is cut.

FIG. 2 corresponds to a moment where, the empty gel card 10 having previously been inserted into the recess 110, one begins to move the tray 108 horizontally toward the housing 102, in the direction symbolized by the arrow F1.

One of the ends of the intake tray 108 comprises a recess 110 designed to receive a receptacle, and in particular the gel card 10 of FIG. 1. More specifically, the gel card 10 is positioned in the recess 110 such that the upper wall 12a and the cover 18 emerge above the horizontal plane of the intake tray 108.

Furthermore, the uncovering station 100 includes a plurality of cutting members 112 which in this case are made up of five small circular saws 112 provided with sharp teeth 113. The saws 112 are coaxial and equidistant. They are rotatably mounted around a horizontal axis A orthogonal to the direction of movement F1 of the tray 108.

Each of the saws 112 is positioned axially (relative to the axis A) in a vertical plane passing between two adjacent holes of the gel card. The axial distance between two adjacent saws is substantially equal to the distance d between holes. Furthermore, as shown in FIG. 2, the saws are positioned above the gel card.

Each of the five saws 112 is designed to produce a cut in the cover 18 of the gel card 10 between two adjacent holes, during the movement of the tray 108 toward the housing 102. As better seen in FIG. 3, the saws 112 therefore make it possible to simultaneously form six cover portions $120_1$, $120_2$, $120_3$, $120_4$, $120_5$, $120_6$ separated from one another, each of said cover portions covering one of the holes 14 of the gel card 10.

Furthermore, in order to avoid the risk of pushing back of the material making up the cover, which would tend to stiffen the cover, it is preferable to cut the cover while removing the material. To that end, the direction of rotation S of the saws is preferably opposite the direction of movement F1 of the tray 108 toward the housing 102.

Preferably, the saws are positioned such that the ends of the sharp teeth 113 come into contact with the plastic upper wall 12a of the body of the gel cards 10. To avoid the formation of plastic shavings, the teeth advantageously have pointed ends.

Figure 3:
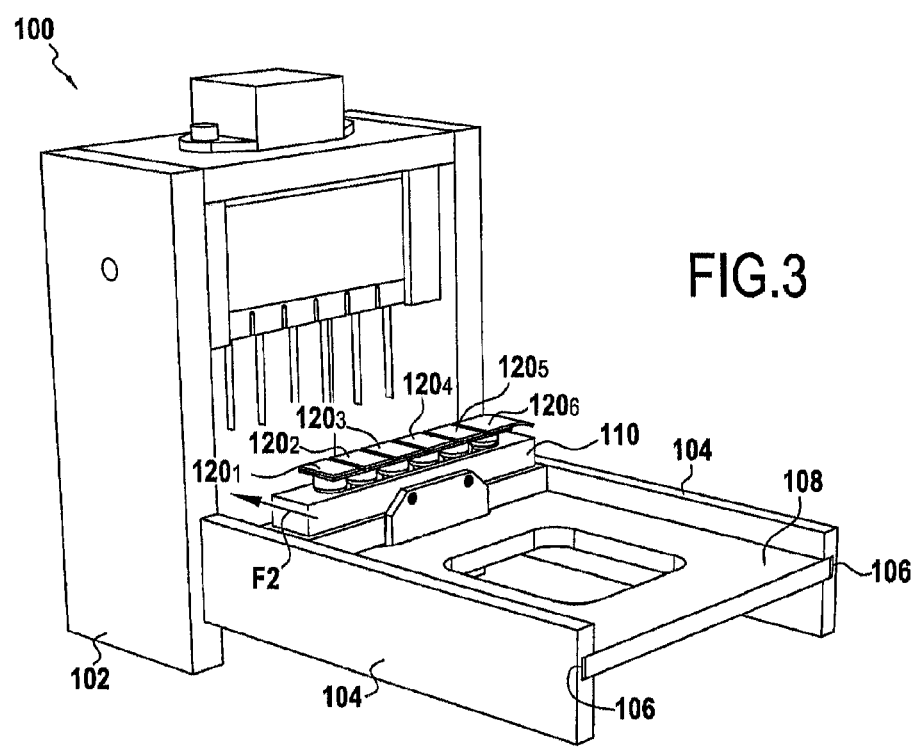
FIG. 3 illustrates the uncovering station of FIG. 2, before the cutting operation of the cover, at the end of which six cover portions have been formed.

After the cutting operation, as illustrated in FIG. 3, the tray 108 is moved in the direction referenced F2 so as to position the gel card 10 in the housing 102.

Figure 4:
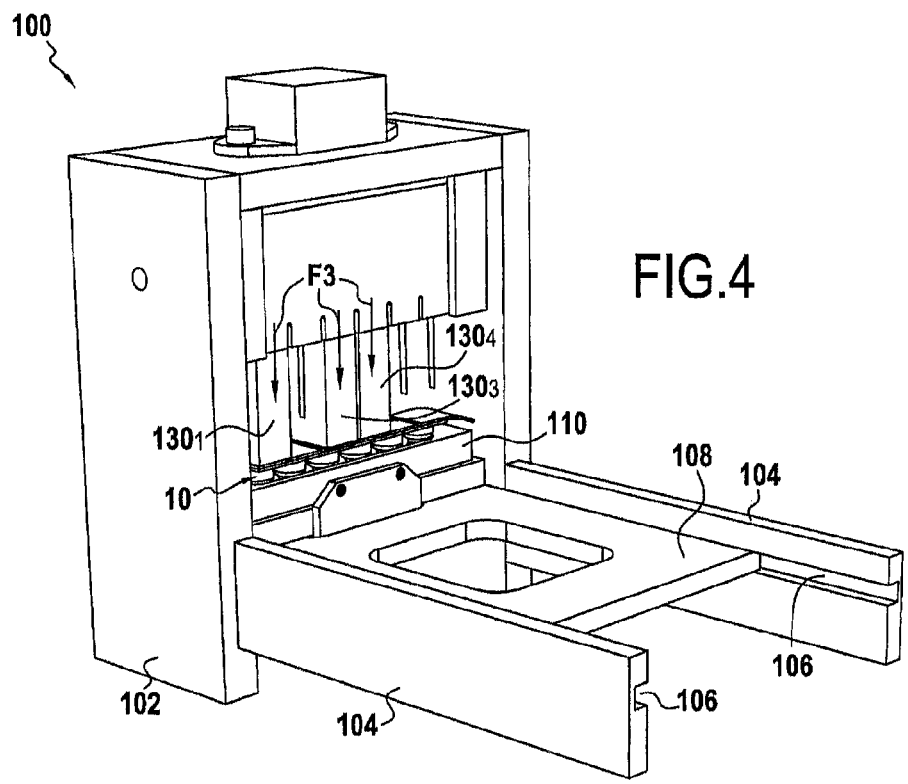
FIG. 4 illustrates the uncovering station of FIG. 3, after the operation for forming the cover portions, three gripping devices being brought into the working position so as to keep the three cover portions covering the three selected holes.
Figure 5:
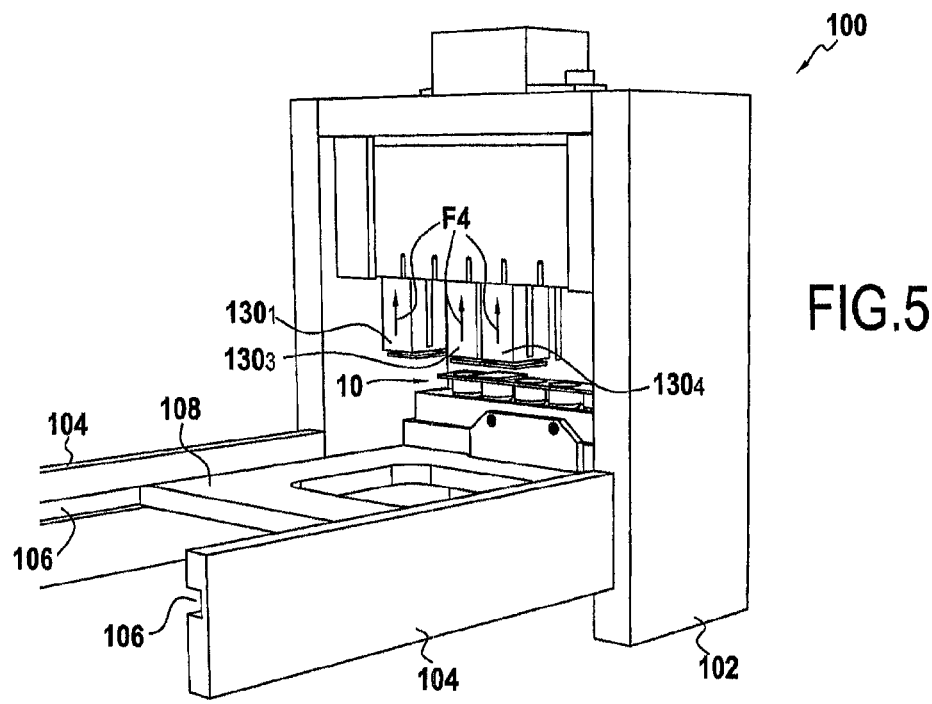
FIG. 5 illustrates the opening of the three selected holes.
Figure 6:
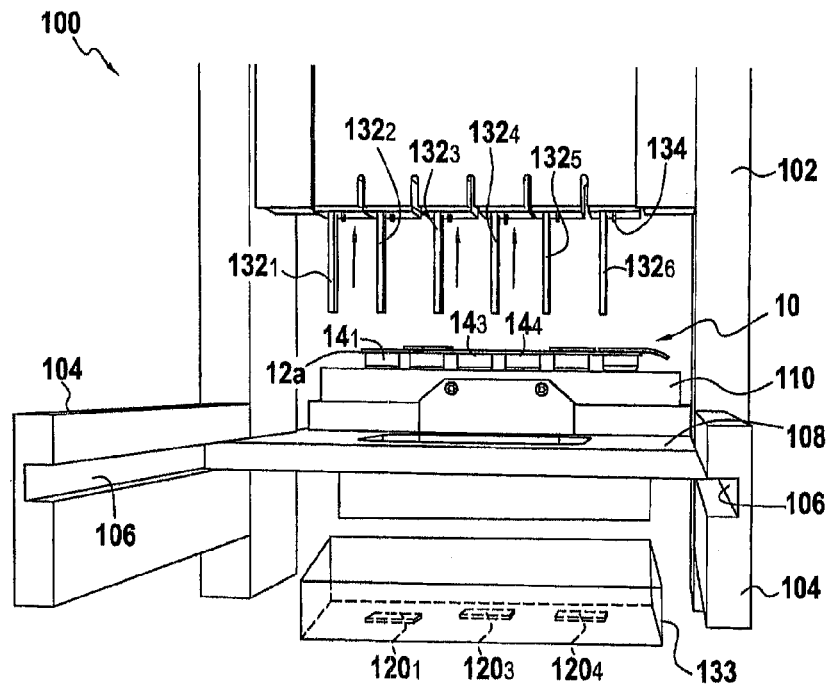
FIG. 6 illustrates the raising of the three gripping devices and the removal of the three cover portions.
Figure 7:
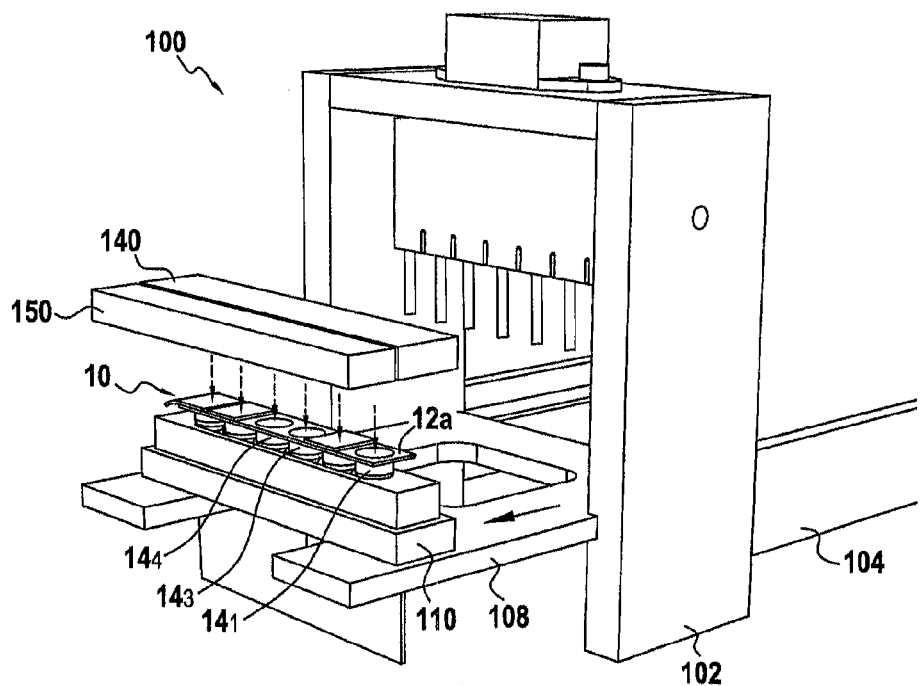
FIG. 7 illustrates the step during which it is verified that the selected holes have been correctly opened.

FIGS. 4 and 5 will now be used to describe how the uncovering operation is carried out.

In this example, a decision is made to open the holes $14_1$, $14_3$ and $14_4$. This choice is completely arbitrary and, of course, it may be decided to open only one of the holes or any other combination of holes.

The holes $14_1$, $14_3$ and $14_4$ that one wishes to open are called the selected holes. These selected holes $14_1$, $14_3$ and $14_4$ are therefore covered by the cover portions referenced $120_1$, $120_3$ and $120_4$.

According to the invention, the uncovering station 100 includes a plurality of heating gripping devices 130, each of said devices being arranged to be able to heat and remove a cover portion.

In this example, the heating gripping devices assume the form of studs that can be moved vertically, independently of one another, but not necessarily simultaneously. In the case at hand, the station includes six studs that are positioned across from each of the holes 14 of the gel card 10, and therefore across from each of the cover portions.

Each stud 130 has an idle position, as well as a working position in which said stud is made to bear against a cover portion, i.e., here bearing against the upper wall 12a of the body 12 of the gel card 10.

As will be seen below, the studs are heated beforehand before being brought into the working position.

In the example of FIG. 4, the heating studs $130_1$, $130_3$ and $130_4$ are positioned vertically along the arrow F3 to be made to bear respectively against cover portions $120_1$, $120_3$ and $120_4$.

The heat given off by the heating studs $130_1$, $130_3$ and $130_4$ causes the heat-sealing film or the glue positioned between the cover portions and the upper wall 12a of the body of the gel card to melt, following which the cover portions $120_1$, $120_3$ and $120_4$ come unglued from the gel card. The selected holes $14_1$, $14_3$ and $14_4$ have thus been opened (uncovered).

In this example, the cover portions are removed by bringing the heating studs $130_1$, $130_3$ and $130_4$ back toward their idle position, in other words by moving vertically in the direction symbolized by the arrow F4 (opposite the arrow F3) of FIG. 5. It has been observed that the cover portions are carried away by the studs when the latter rise. However, it is preferable, but not essential, to provide heating studs with means 134 for gripping the cover portions, said means for example being able to assume the form of small claws or tips 134.

After the uncovering operation, it is desirable to discharge the cover portions $120_1$, $120_3$ and $120_4$ that may have remained attached to the heating studs $130_1$, $130_3$ and $130_4$. To that end, the station according to the invention includes several discharge members for expelling the cover portions gripped by the heating stud. In the case at hand, the station includes six discharge members made up of six rods referenced $132_1$, $132_2$, $132_3$, $132_4$, $132_5$ and $132_6$. These rods are fixed to the housing 102 and are positioned such that the gripping devices (the studs) slide around said rods. As will be understood using FIGS. 4 and 6, the rods are completely housed in the heating studs when the latter are in their working position, and protrude when the heating studs are brought back to the idle position. Thus, when the heating studs $130_1$, $130_3$ and $130_4$ rise, the rods $132_1$, $132_3$ and $132_4$ expel the cover portions $120_1$, $120_3$ and $120_4$ which, in this example, next fall into a collection tub 133.

After the uncovering operation, the tray 108 is moved so as to bring the gel card 10 near means 140 for verifying whether the selected holes $14_1$, $14_3$ and $14_4$ have been correctly opened. In this example, these means are made up of a set of optical sensors that are arranged to be positioned above the upper wall. These sensors are capable of detecting the absence of metal cover portions and therefore the opening of the selected holes. It is, however, possible to provide non-optical verification means.

Furthermore, the station includes at least one ionizer 150 for ionizing the selected holes, after they are opened, in order to eliminate the electrostatic charges that may be contained in the holes.

In reference now to FIGS. 8 to 10, an embodiment of the selection mechanism 200 according to the invention will be described that makes it possible to select the gripping devices (studs) 130 needing to be moved to their working position, as well as the movement device 300 making it possible to move the gripping devices (studs) 130 between their idle position and their working position.

Figure 8:
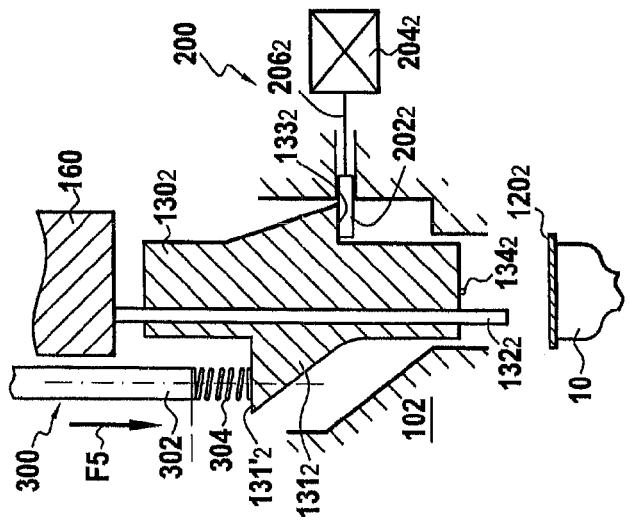
FIG. 8 is a cross-sectional view of one of the gripping devices in the idle position.

FIG. 8 shows one of the heating studs 130 in the idle position, according to a view in a vertical cutting plane parallel to the direction of movement of the tray 108.

In the idle position, the heating stud 130 is in contact with a heating baseplate 160 that is fixed to the housing 102. This heating baseplate for example includes electrical resistances making it possible to keep it at a substantially constant temperature.

In this example, the heating step 130 therefore does not include internal heating means. In other words, the heating stud 130 captures the heat energy when it is in the idle position.

The heating baseplate 160 is configured such that the heating stud can be brought quickly to a temperature of approximately 200° C. To that end, the heating stud will preferably be made from a material such as bronze, or any other material that is a good conductor while having a good friction coefficient.

As already mentioned above, the heating stud 130 ($130_1$, $130_2$) is mounted sliding around the rod 132 ($132_1$, $132_2$), the latter being fixed to the frame 102.

This stud 132 is moved vertically using the movement device 300, which includes a vertically movable plate 302, the lower end of which bears a compression spring 304. The latter exerts pressure against a horizontal bearing surface 131' ($131'_1$, $131'_2$) belonging to a radial extension 131 ($131_1$, $131_2$) of the heating stud 130.

Figure 9:
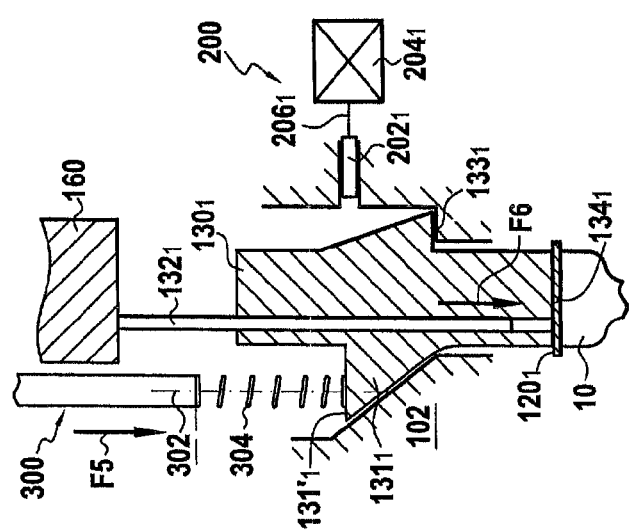
FIG. 9 is a cross-sectional view of one of the gripping devices in the working position.

When the vertical axis 302 is moved vertically toward the gel card, which is symbolized by the arrow F5 in FIG. 9, the spring 304 exerts pressure on the bearing surface 131', which results in vertically moving this stud toward the gel card 10, in the direction indicated by the arrow F6, in order to bring it into its working position in which it is in contact with the cover portion 120.

The selection mechanism includes several fingers 202 ($202_1$, $202_2$) that are transversely movable relative to the direction of movement of the studs 130, between a retracted position and a deployed position. More specifically, in this example, there are as many moving fingers as there are heating studs.

Figure 10:
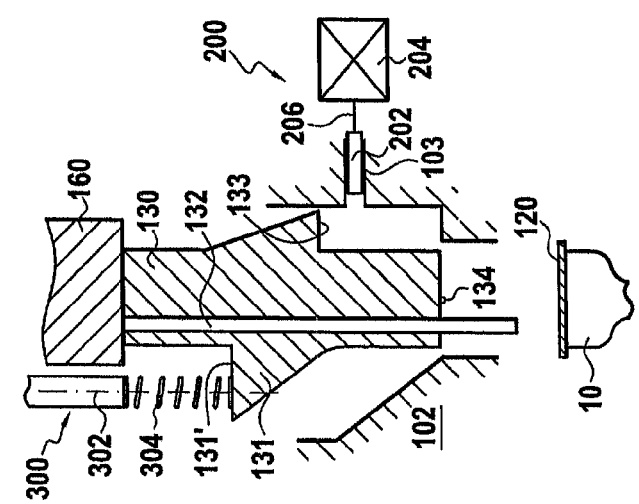
FIG. 10 is a cross-sectional view of one of the gripping devices, the movement of which has not been allowed by the selection mechanism.

FIGS. 8 to 10 show that the movement of the fingers 202 ($202_1$, $202_2$), in this case a horizontal translation, is done using an electromagnet 204 ($204_1$, $204_2$) connected to the finger using a rod 206 ($206_1$, $206_2$).

The stud 130 includes a horizontal stop surface 133 ($133_1$, $133_2$) designed to cooperate with the finger 202 ($202_1$, $202_2$) when the latter is in its deployed position, as shown in FIG. 10.

Thus, when the finger is in the retracted position, as is the case in FIG. 9, the stud $130_1$, which is then a selected stud, may be brought into the working position by vertical movement of the plate 302, the finger $202_1$ not opposing the movement of said stud.

However, when the finger $202_2$ is in the deployed position, as is the case in FIG. 10, the stop surface $133_2$ of the stud $130_2$ comes in contact with the finger $202_2$ during movement of the plate 302. This results in blocking the movement of the stud $130_2$, which is therefore not selected, and subsequently preventing it from being brought into the working position.

In the example of FIGS. 8 to 10, the movement of the plate 302 causes simultaneous movement of all of the studs during the uncovering operation. However, only the studs for which the associated finger is in the retracted position (the selected studs) are brought into the working position. In other words, it is understood that the selection mechanism makes it possible to prevent the movement of the studs that are not selected.

It will therefore be understood that the invention allows selective opening of the holes of the gel card, automatically.

The embodiments or examples described in the present description are provided as an illustration and non-limitingly, one skilled in the art easily being able, in light of this description, to modify these embodiments or example embodiments, or to consider others, while remaining within the scope of the invention.

Furthermore, the different features of these embodiments or examples may be used alone or in combination with each other. When they are combined, these features may be combined as described above or differently, the invention not being limited to the specific combinations described herein. In particular, unless otherwise specified, a feature described in relation with one embodiment or example may be applied similarly to another embodiment or example.

The invention claimed is:

1. A station for uncovering a receptacle including a body in which several adjacent holes initially sealed by a cover are formed, including:
   a plurality of coaxial and equidistant blades or saws, wherein each blade or saw is (i) rotatably mounted around a horizontal axis orthogonal to a direction of movement of the receptacle, and (ii) is positioned axially in a vertical plane passing between two adjacent holes of the receptacle, and (iii) an axial distance between two adjacent blades or saws is equal to a distance between adjacent holes of the receptacle, and wherein at least one blade or saw is configured to make at least one cut in the cover between two adjacent holes, so as to divide the cover into portions, each cover portion covering at least one of the holes of the receptacle, at least one of the holes of the receptacle being a selected hole covered by a selected cover portion; and
   at least one heating gripping device that is arranged to heat and remove the selected cover portion, thereby opening the selected hole.

2. The station according to claim 1, including a plurality of blades or saws, each of the blades or saws being able to produce a cut in the cover between two adjacent holes so as to form one or more cover portions covering one or more holes.

3. The station according to claim 1, including a plurality of gripping devices that can be moved independently of one another, each of the gripping devices having an idle position in which said gripping device is heated by a heating device, and a working position in which the heated gripping device is brought to bear against at least one of the cover portions.

4. The station according to claim 3, further including a plurality of fingers for selecting the gripping device(s) needing to be moved toward the working position, and a moving plate for moving said selected gripping device(s) toward the working position.

5. The station according to claim 4, wherein each gripping device is fastened to the plate using a spring designed to exert a pressure force on the gripping device oriented toward the body of the receptacle, and the plurality of fingers are arranged to prevent the movement of the gripping devices that are not selected.

6. The station according to claim 3, wherein the heating device includes a fixed heating baseplate and in that, in the idle position, each gripping device is in contact with said heating baseplate.

7. The station according to claim 3, wherein each gripping device comprises claws or tips for gripping one of the cover portions, and the station furthermore includes at least one rod for expelling said cover portion gripped by the gripping device.

8. The station according to claim 7, where the gripping device slides around the rod, said rod being arranged to expel the cover portion when the gripping device is returned to the idle position.

9. The station according to claim 1, further including a set of optical sensors to verify whether the selected hole has been correctly opened.

10. The station according to claim 1, further including an ionizer to ionize the selected hole(s) after opening thereof.

11. A biological sample analysis installation including an uncovering station according to claim 1 designed to uncover gel cards including reagent holes.

* * * * *

UNITED STATES PATENT AND TRADEMARK OFFICE
CERTIFICATE OF CORRECTION

PATENT NO. : 9,658,141 B2
APPLICATION NO. : 14/004111
DATED : May 23, 2017
INVENTOR(S) : Sébastien Bernay et al.

It is certified that error appears in the above-identified patent and that said Letters Patent is hereby corrected as shown below:

On the Title Page

Assignees section, "MAMES LA COQUETTE, FR" should read --MARNES LA COQUETTE, FR--.

Signed and Sealed this
Twenty-fifth Day of July, 2017

Joseph Matal
*Performing the Functions and Duties of the
Under Secretary of Commerce for Intellectual Property and
Director of the United States Patent and Trademark Office*